United States Patent [19]

McRae

[11] Patent Number: Plant 6,697

[45] Date of Patent: Mar. 28, 1989

[54] HYBRID LILY PLANT NAMED SUN PIXIE

[75] Inventor: Edward A. McRae, Boring, Oreg.

[73] Assignee: Melridge, Inc., Gresham, Oreg.

[21] Appl. No.: 101,492

[22] Filed: Sep. 28, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid lily plant bearing large clusters of flowers of large size and excellent form particularly characterized by their rich orange coloration, accented by a golden orange band along the midrib. This plant is of short stature, about fourteen to eighteen inches in height, and has an abundant foliage of medium sized leaves, and a vigorous growth habit. The moderately short stature of the plant, its full leaves, and its large sized flowers make it especially suitable as a pot plant variety; its color pattern and silhouette being completely new in the upright Asiatic divisions of lilies suited to forcing and to mass commercial cultivation. The plant is highly resistant to disease and shows high tolerance of virus. It is an excellent garden plant and the bulbs may be precooled and forced throughout the year for pot plant production.

1 Drawing Sheet

BACKGROUND OF THE NEW PLANT

My new variety of lily plant originated as a seedling selected from a group of seedlings planted by me at Sandy, Oreg., with the object of producing lilies having flower shades of orange and yellow and well suited to forcing for pot plant production out-of-season.

This selected seedling resulted from my crossing of the clonal cultivar 'Charisma' (U.S. Plant Pat. No. 4,180) as the seed parent with a unique hybrid clone or short stature named 'Honeybear' (unpatented) as the pollen parent. The present seedling was selected for propagation because of the exceptionally large size of its flowers and the rich orange coloration of the tepals accented by a golden orange midrib band and an attractive "ring" of spots encircling the center of the flower, this combination being unique in this type of lily. Accordingly, this selected seedling was asexually reproducedby me at Sandy, Oreg., with such pleasing results that continued propagation of this new variety was carried on by me and under by direction through several successive generations by bulb scale propagation and by natural propagation from bulblets, which demonstrated that the novel and distinctive characteristics of my new variety are fixed and hold true, under asexual propagation, from generation to generation.

This new variety remains relatively short and is not overly susceptible to bud abortion when forced into flower out-of-season as a pot plant. Additionally, the clone appears to possess to a high degree the desirable characteristics of hybrid vigor, great hardiness, and disease resistance, possessing all of the desired characteristics of excellence of form, color and habit, and the clone is vigorous and a good grower and propagator, as observed at Sandy, Oreg.

This new variety is also well suited to forcing out-of-season when the bulbs are dug at the appropriate time and properly precooled. For example, October-dug bulbs, properly precooled and potted in January, will flower under glass in western Oregon in an average of sixty-five to seventy-five days with no supplemental lighting and at moderate greenhouse temperatures.

DESCRIPTION OF THE DRAWING

This new variety of lily plant is illustrated by the accompanying drawing which shows the open blooms in full color, illustrating the flower form and tepal arrangement and the novel and distinctive rich orange flower coloration with a golden orange midrib on each of the tepals, the colors shown being as nearly true to those herein specified as is reasonably possible to obtain by conventional photographic proceduers.

DESCRIPTION OF THE NEW VARIETY

The following is a detailed description of my new variety of Asiatic hybrid lily with nomenclature according to The International Lily Register, Second Edition, 1969, by The Royal Horticultural Society of London, England, and with color designations according to The R.H.S. Colour Chart published by the society in 1966.

THE PLANT

Origin: Seedling.

Parentage:

*Seed parent.*—Lilium 'Charisma' (U.S. Plant Pat. No. 4,180).

*Pollen parent.*—Lilium 'Honeybear' (unpatented).

Classification:

*Horticultural.*—Division I-A, Upright Asiatic Hybrid Lily, according to The Horticultural Classification of Lilies (The Royal Horticultural Society of London, England).

*Commercial.*—Hybrid Lilium Clone.

Form: A single stem, erect and stately.

Height: About 35 to 45 cm. on stems produced by glasshouse forcing of bulbs of about 15 to 18 cm. in circumference, provided that their light levels are adequate; low light levels may result in "stretching".

Growth: Vigorous and upright.

Foliage:

*Quantity.*—Abundant.

*Leaf size.*—About 6 to 10 cm. long and about 0.5 to 0.8 cm. wide.

*Leaf shape.*—Lanceolate with acuminate tip.

*Texture.*—Leathery and glabrous.

*Aspect.*—Glossy.

*Color.*—Dark green on the upper side; somewhat lighter on the lower side.

The bulbs:

*Size.*—Various, ranging to 25 cm. in circumference in commercial use.

*Color.*—White.

THE BUD

Form: Long ovoid with obtuse apex.

Size: About 8 to 9 cm. long and about 6 to 7 cm. in circumference just prior to opening.

Color: Buff Orange, RHS 30 D, overlayed with soft green along the midrib, just prior to opening and as the tepals begin to unfurl.

Opening rate: The bud opens slowly, taking about one hour in response to morning light.

Peduncle:

*Length.*—Averages about 4 to 6 cm., but may elongate if the light levels are too low or if the bulbs have been improperly stored prior to forcing.

*Color.*—Deep green with soft plum overlay.

THE FLOWER

Blooming habit: Once annually and profusely in midseason.

Size: Large, averaging about 15 to 19 cm. in diameter.

Borne: In a single compact raceme inflorescence, producing about five to eight buds from a bulb of about 12 to 18 cm. in circumference.

Shape: Cup-shaped when first opening and becoming flattened as the tepals recurve during the second day.

Tepalage:

*Number.*—Six.

*Arrangement.*—Hexagonal with the inner tepals alternating between the lower tepals.

*Shape.*—Obovate with entire margins and acuminate tip.

*Appearance.*—Shiny.

*Size.*—The outer tepals average about 3 cm. wide and the inner tepals average about 4 to 4.5 cm. wide.

*Color.*—The base color is a rich Orange, RHS 28 A to 30 B, and there is a band of Golden Orange, RHS 25 B, about 1 cm. wide extending for about 4 cm. from the nectaries along the midrib of each tepal. The nectaries are of a soft orange color but they are covered with short, white pubescence. The outer tepals have lightly frilled margins.

*Spotting.*—The basal third of the inner tepals only is marked with about ten to fifteen small, magenta purple spots scattered about the midrib just above the nectaries.

*Tepal longevity.*—The tepals stay on the stems for about three weeks.

Color changes: The flower color deepens to RHS Orange-Red, 32 B-C, as the flower ages, if the light levels are adequate for cut flower and pot plant maintenance.

Appearance: The flower is shiny.

Fragrance: None.

Lasting quality: The flower is long lasting, both on the plant and as a cut flower.

Disease resistance: The flower and plant are resistant to disease; particularly they are resistant to Fusarium Bulb Rot and to Botrytis Blight, as observed in western Oregon.

Pedicel:

*Length.*—Averages about 5 to 10 cm.

*Color.*—Dark green with a light plum overlay.

*Character.*—Sturdy and ascending up to about 30° from the horizontal and rarely has secondary buds.

THE REPRODUCTIVE ORGANS

Stamens:

*Number.*—Six.

*Arrangement.*—Typical of the genus Lilium.

*Pollen and anthers (dehisced).*—Greyed Red, RHS 171A.

*Filaments.*—Length: About 5 cm. Color: Soft Orange, RHS 28 B-C.

Pistil:

*Number.*—One.

*Style.*—Length: About 5 cm.

*Stigma.*—Color: Soft orange with plum overlay, RHS Greyed Red, 180 A-B.

Character of ovary: The ovary is characteristic of the genus Lilium.

THE FRUIT

Fertility: The fruit is fertile.

Shape: Ovoid.

Color at maturity: Soft brown, sometimes overlaid with soft plum.

This new lily variety most closely resembles 'Irish Pixie' but has larger flowers with a longer, golden orange "ray" on each tepal and only the outer tepals bear any spots. The new plant has longer and narrower leaves than 'Irish Pixie' and has glabrous buds and upper leaves.

I claim:

1. The new and distinctive variety of Asiatic hybrid lily plant and parts thereof, substantially as herein shown and described, characterized by its relatively short stature and its large, rich orange flower coloration, the tepals of the flowers being accented by a light colored orange midrib band.

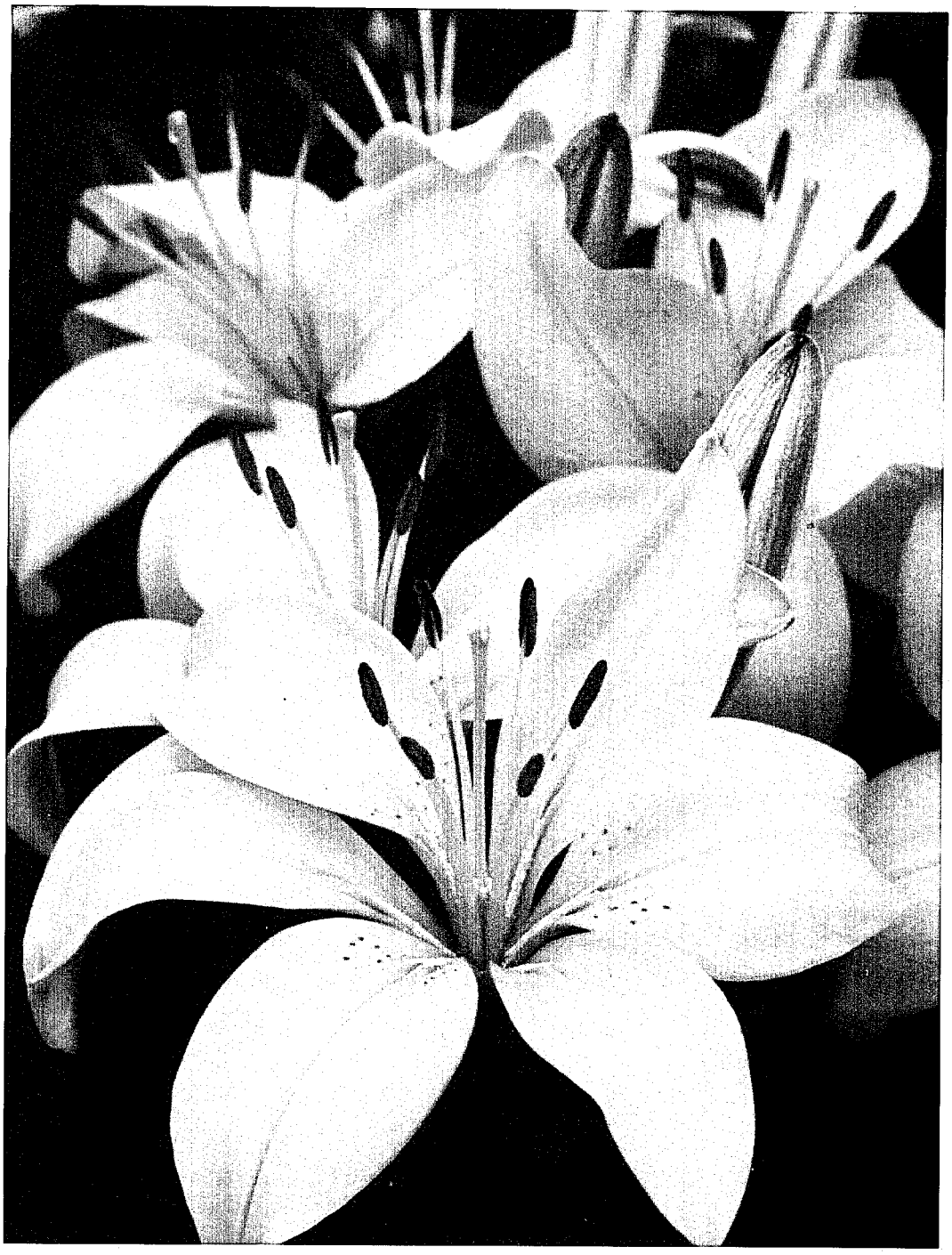

* * * * *